United States Patent [19]

Brown et al.

[11] Patent Number: 5,173,085
[45] Date of Patent: Dec. 22, 1992

[54] HAIR DYEING PROCESS AND COMPOSITONS PACKAGE

[75] Inventors: Keith Brown, New Canaan; Bryan P. Murphy, Trumbull; Leszek J. Wolfram, Stamford, all of Conn.

[73] Assignee: Clairol Incorporated, Stamford, Conn.

[21] Appl. No.: 649,132

[22] Filed: Jan. 29, 1991

Related U.S. Application Data

[63] Continuation of Ser. No. 348,106, Apr. 28, 1989, abandoned, which is a continuation of Ser. No. 712,465, Mar. 15, 1985, abandoned, which is a continuation of Ser. No. 447,557, Dec. 7, 1982, abandoned.

[51] Int. Cl.$^5$ .............................................. A62K 7/13
[52] U.S. Cl. ......................................... 8/405; 8/406; 8/425; 8/429; 8/431; 8/433; 8/435
[58] Field of Search ................... 8/405, 406, 425, 429, 8/431, 433, 435

[56] References Cited

U.S. PATENT DOCUMENTS

| | | | |
|---|---|---|---|
| 2,539,202 | 1/1951 | Peck | 8/406 |
| 2,875,769 | 3/1959 | Rosmarin et al. | 8/406 |
| 2,934,396 | 4/1960 | Charle et al. | 8/423 |
| 3,194,734 | 7/1965 | Seemuller et al. | 8/423 |
| 3,215,605 | 11/1965 | Soloway | 8/425 |
| 3,698,852 | 10/1972 | Pantzer et al. | 8/408 |
| 3,993,436 | 11/1976 | Fujinuma | 8/424 |

FOREIGN PATENT DOCUMENTS

| | | | |
|---|---|---|---|
| 2028818 | 12/1970 | Fed. Rep. of Germany . | |
| 0072836 | 6/1978 | Japan | 8/429 |
| 130443 | 11/1978 | Japan . | |
| 53-133641 | 11/1978 | Japan . | |
| 11240 | 1/1979 | Japan . | |
| 797174 | 6/1958 | United Kingdom | 8/424 |
| 887579 | 1/1962 | United Kingdom | 8/424 |

OTHER PUBLICATIONS

"Instrumental Measurement and Control of Colour" Author: T. F. Chong, Rev. Prog. Coloration vol. 18 (1988) pp. 47-55.

Primary Examiner—Frederick E. Waddell
Assistant Examiner—Zohreh A. Fay
Attorney, Agent, or Firm—Charles J. Zeller

[57] ABSTRACT

A hair dyeing process which comprises of steps of contacting the hair to be dyed with an aqueous solution of a metal salt that promotes melanogenses in air. Before or after the aforementioned step contacting the hair with a solution of 5,6-dihydroxyindole, rinsing the hair between the two contacting steps, maintaining the contact with the second-used solution until a desired darker color is obtained, rinsing or shampooing the hair, then contacting the hair with a solution of hydrogen peroxide until the desired color shade is obtained, and then again rinsing the hair.

21 Claims, No Drawings

HAIR DYEING PROCESS AND COMPOSITONS PACKAGE

This is a continuation of U.S. Ser. No. 07/348,106 filed Apr. 28, 1989, now abandoned, which is a continuation of abandoned application U.S. Ser. No. 06/712,465 filed Mar. 15, 1985, which is a continuation of abandoned application U.S. Ser. No. 06/447,557 filed Dec. 7, 1982 now abandoned.

FIELD OF THE INVENTION

The present invention relates to a process for dyeing hair, particularly human hair, and composition package for carrying out that process.

BACKGROUND OF THE INVENTION

The color of human hair is due to the presence within its structure of discrete natural pigment particles—the melanins. The study of melanins and melanogenesis has intensified in the last 40 years, accompanied by some interest in the dyeing of hair with such materials that most closely resemble the natural materials which contribute the color to hair. The biosynthesis of melanin involves conversion of tyrosine via dihydroxyphenylalanine (dopa) to melanin through a number of intermediate steps, including 5,6-dihydroxyindole, to melanin.

In addition to the general desirability of dyeing hair in a simple fashion and with a dye which is the closest to the material that contributes the natural coloration of hair, a requirement also exists for a hair colorant which can also serve, if desired, as a temporary hair color which can be applied and removed at will and which can be applied in a reliable and fast manner.

SUMMARY OF THE PRIOR ART

Patents issued which cover aspects of hair coloring with melanin precursors, e.g. tyrosine, L-dopa, L-dopa esters, and 5,6-dihydroxyindole. U.S. Pat. Nos. 2,539,202; 2,875,769; and 3,698,852 deal with using L-dopa as the starting material. U.S. Pat. Nos. 2,934,396; 3,194,734; and 3,993,436 disclose the use of 5,6-dihydroxyindole as the starting material. The major disadvantages of these systems are the time required for color development, the uncertainty of the development and the lack of control over it, and the necessity of adding compounds such as p-phenylenediamine and various couplers for shade adjustment.

In the process disclosed in U.S. Pat. No. 2,934,396 hair is first treated with an acidic or neutral solution of 5,6-dihydroxyindole, then the excess solution is blotted off and an oxidizing agent or an oxidation-inducing solution is applied to the hair until the desired shade is developed. In one of the methods disclosed in the patent the oxygen of the ambient air is utilized wherein the second solution contains an alkalizer and a cobalt or manganese oxidation promoter. Mainly, however, an ammoniacal solution of an oxidizing agent, such as of hydrogen peroxide or an alkali metal or ammonium iodate, periodate or persulfate, etc. is taught to be employed. When the desired shade is developed, the hair is rinsed, shampooed, rinsed again and dried.

U.S. Pat. No. 3,194,734 is characterized as an improvement over the above-mentioned U.S. Pat. No. 2,934,396, because in the process of the earlier patent the dyeing which is the oxidative polymerization of the 5,6-dihydroxyindole into melanin simultaneously competes with an oxidative destruction of the dye that is being formed, resulting in a waste of indole, producing uneven results on the hair and it is difficult to determine when to stop the process by rinsing. Therefore, this later patent proposes a process wherein an aqueous alkaline composition containing 5,6-dihydroxyindole and ammonia or an amine are used to contact the hair until the desired shade is obtained. Alternatively, certain methyl derivatives of 5,6-dihydroxyindole can be employed in a two step process to obtain lighter shades wherein the hair is first impregnated with an aqueous solution of such a methyl derivative in an acidic or neutral pH solution, then is briefly dried and then the color is developed in a second step by application of an aqueous solution containing an oxidizing agent.

DETAILED DESCRIPTION OF THE INVENTION

The present invention is, in part, based on the discovery that, in contrast to the prior art where $H_2O_2$ or other oxidants are used either in a separate step, or together with the 5,6-dihydroxyindole, to obtain a variety of shades, superior results can be obtained by utilizing a metal salt for promoting melanogenesis.

We discovered that a better variety of shades and more reliable shade development and, if desired, improved temporary hair coloring can be achieved by a hair dyeing process which comprises the steps of contacting the hair to be dyed with a solution, suitably aqueous solution, of a metal salt which promotes melanin formation from 5,6-dihydroxyindole, before or after the aforementioned step contacting the hair with a solution, suitably aqueous solution, of 5,6-dihydroxyindole, rinsing the hair between the two contacting steps, maintaining the contact with the second-used solution until a desired darker color is obtained, rinsing or shampooing the hair, then contacting the hair with a solution of hydrogen peroxide for a maximum of 15 minutes until the desired color shade is obtained, and then again rinsing the hair.

In a particularly suitable embodiment of the process of the present invention the process comprises the steps of contacting the hair to be dyed with an alkaline solution, suitably an aqueous solution, containing cupric ions, before or after the aforementioned step containing the hair with a solution, suitably aqueous solution, of 5,6-dihydroxyindole, rinsing the hair between the two contacting steps, maintaining the contact with the second-used solution until a desired darker color is obtained, and rinsing or shampooing the hair. If a color other than grey or black is desired, the shade is obtained with a subsequent treatment with $H_2O_2$. Thus, it can be seen that a principal distinction of the present process over all prior proposals for dyeing with 5,6-dihydroxyindole is that in all cases, except when the desired ultimate color is black, the hair is first dyed to a grey or black color, and the ultimate desired shade is subsequently developed by lightening with the hydrogen peroxide solution.

A further feature of the present invention is a hair dyeing kit which includes in a single package a plurality of containers, comprising a first container including therein an aqueous alkaline pH solution of an effective amount of a metal which promotes melanin formation from 5,6-dihydroxyindole, a second container including therein a solution of 5,6-dihydroxyindole at an acidic pH, a vapor space being maintained above the solution in said second container and containing a non-oxidizing gas in said space, a third container including therein an alkalizer, said vapor space in said second container being of sufficient volume to accept said third container or the contents of said third container with said vapor space, and a fourth container which contains a solution of hydrogen peroxide.

In a further feature the present invention provides a hair dyeing kit which includes in a single package a plurality of containers, comprising a first container including therein an aqueous alkaline pH solution of an effective amount of a metal which promotes melanin formation from 5,6-dihydroxyindole, a second container including therein an alkaline solution, a vapor space being maintained above the solution in said second container, a third container including therein a solution of an effective amount of 5,6-dihydroxyindole at acidic pH, said vapor space in said second container being of sufficient volume to accept said third container or the contents of said third container within said vapor space, and a fourth container which contains a solution of hydrogen peroxide.

In yet another embodiment of the invention a hair dyeing kit is provided which includes in a single package a plurality of containers, comprising a first container including therein an alkaline pH solution containing an effective amount of copper, a second container including therein a solution of an effective amount of 5,6-dihydroxyindole at an acidic pH, a vapor space being maintained above the solution in said second container and containing a non-oxidizing gas in said space, and a third container including therein an alkalizer, said vapor space in said second container being of sufficient volume to accept said third container or the contents of said third container within said vapor space.

A further embodiment of the invention is a hair dyeing kit which includes in a single package a plurality of containers, comprising a first container including therein an alkaline pH solution containing an effective amount of copper, a second container including therein an alkaline solution, a vapor space being maintained above the solution in said second container, and a third container including therein a solution of an effective amount of 5,6-dihydroxyindole at acidic pH, said vapor space in said second container being of sufficient volume to accept said third container or the contents of said third container within said vapor space.

In accordance with the present invention, unless a black or grey shade is desired, the hair dyed with the melanin from 5,6-dihydroxyindole is lightened with a hydrogen peroxide-containing solution. As used throughout the specification and the claims, the term "hydrogen peroxide" intends to denote hydrogen peroxide or any other ingredient which is an aqueous solution forms hydrogen peroxide, such as urea peroxide. This lightening or color shade-establishing step is different from the conventional oxidizing treatment employed in the conventional bleaching of hair. In conventional bleaching the natural color of hair is removed by bleaching when it is desired to color it to a shade that is lighter than the natural color of the hair. In that case the natural color of the hair is bleached out over a longer period of time with a strong oxidizing solution which usually contains hydrogen peroxide and additional bleach boosting persalts, around pH 10. This bleaching step generally tends to weaken or otherwise damage the hair. In the lightening step of the present invention we do not deal with the conventional kind of bleaching, because the hydrogen peroxide solution used in the present invention does not contain added bleach boosters such as persalts, it is suitably employed at a pH below 10, suitably around 9, and the lightening requires only up to about 15 minutes for the lightest shades. Hence the lightening, color-developing oxidizing step of the present invention is considerably faster than conventional bleaching and is not employed to carry the lightening further than the natural color of the hair or the color that it had before the process of this invention was employed. As used throughout the specification and the claims the term "hair" is intended to refer to human hair.

Without intending to be bound by the following explanation, we believe that the difference in the lightening in accordance with the present invention and conventional bleaching is attributable to the new dyeing step of the present invention. In naturally colored hair the melanin pigment is distributed throughout the cortex, i.e. the inner core of the hair shaft. This means that in bleaching the natural melanin color in hair with a strong bleach, such as hydrogen peroxide as boosted by added persalts, considerable time is required for the bleach to penetrate through the unpigmented periphery or cuticle into the hair shaft. In the process of the present invention the dye is believed to be disposed principally along the periphery of the hair shaft and the lightening hydrogen peroxide does not require the presence of percompound boosters and prolonged exposure to reach and to bleach the dye. Due to the shorter exposure and the peripheral penetration, the lightening step of the present invention does not tend to damage or weaken the hair as is the case in conventional bleaching.

Furthermore, it is believed that the dyes produced in accordance with the present invention are unique in that the melanogenesis-promoting metal forms a complex with the melanin formed during dyeing. The affinity of the complexed metal is viewed as being greater for melanin than for the keratin of the hair. Therefore the reactivity of the melanin-metal complex dye is greater with hydrogen peroxide than that of melanin without the metal. This is borne out by the observation that the melanin/copper complex produced in accordance with the present invention can be lightened faster with hydrogen peroxide than a natural melanin, even if a copper salt is dissolved in the hydrogen peroxide used to lighten the natural melanin. Therefore, the metal not only promotes melanin formation in the dyeing step of the present invention, but is believed to contribute to the ease and rapidity of the lightening step. For this reason we distinguish the lightening step of the present invention which can be completed in under 15 minutes from conventional bleaching which is of a different kind and requires generally a time period that is well over twice as long and requires bleach boosters in addition to hydrogen peroxide.

Accordingly, another feature of the present invention is a complex melanin hair dye as a new composition of matter, said dye being prepared by contacting hair with a solution of 5,6-dihydroxyindole, and before or after the aforesaid step contacting the hair with a solution of a cupric salt.

The process of the present invention can also be used for dyeing hair which was previously dyed with conventional permanent or semipermanent hair dyes. As long as the original dye is stable to the lightening solution that is milder than conventional hair bleaches, the dyeing and lightening steps of the present process do not destroy the starting color of the hair within the times employed herein for lightening, whether or not the starting color is natural color of the hair. Accordingly, hair colored by the present process can be re-lightened to that starting color, whether that re-lightening takes place the next day or a considerable time later.

If the present process is intended to color hair to a shade which is lighter than the natural shade of hair, or lighter than a shade to which hair was dyed by conventional techniques, then the hair has to be first bleached lighter, or even bleached completely, before employing the process of the present invention. In that case the lightening treatment of the present invention can be carried to any shade that is darker than the initially bleached shade, and then the hair can be lightened to any intermediate shade, or if desired, the initially bleached shade can be restored.

If the desired shade is a lighter one, it is not necessary to dye the hair entirely black, but dyeing to a lighter or darker grey will suffice. When the dye is then lightened in a subsequent step, it will initially lighten to a lighter or darker brown shade, depending on whether it was dyed to a lighter or darker grey in the initial steps. Of all the melanogenesis promoters that were tested, only $Cu^{2+}$ was found to promote melanin formation all the way to an intense black color. The other metal promoters that were tested appear to assist dyeing only to lighter or darker shades of grey. In our experiments longer exposure of the hair or larger concentrations of the metal promoter did not result in an increase of the resulting depth of color.

In the dyeing step the treatment of the hair with the solution of the melanogenesis promoter can generally precede or follow the treatment of the hair with the 5,6-dihydroxyindole-containing solution. Generally a better depth of color could be obtained when the treatment with the promoter solution preceded the contacting with the 5,6-dihydroxyindole solution. Any metal or transition metal ion which is capable of promoting melanogenesis is believed to be suitable for that purpose. These include, for example, solutions of iron, cobalt, manganese, copper, silver, titanium, zirconium, tantalum, chromium, nickel, palladium, platinum, gold, mercury, cadmium, zinc, tin, antimony, lead, bismuth, etc. The metal salts can be employed alone or in mixtures. Except for cupric solutions it was found that it is generally necessary to employ a chelating agent such as citric acid, a citrate, ethylenediamine tetraacetic acid, ascorbic acid and the like to keep the metal in solution.

Terms, such as "melanogenesis promoter", "melanogenesis-promoting metal salt" and variants of such terms, as used throughout the specification and the claims intend to refer to solutions of one or more metals which will promote color formation in hair within a maximum period of 20 minutes after the hair was contacted with a solution of 5,6-dihydroxyindole. Whether or not a given metal or a given combination of metals can perform as a melanogenesis promoter, can be determined by routine experimentation by trying out its ability to form a melanin dye in accordance with the process of the present invention.

The melanogenesis promoter which was found most suitable is $Cu^{2+}$ which provides a considerably faster dyeing and the resulting color can go all the way to solid black. While $Fe^{2+}$ ion will also work well, it is less preferred than copper, due to solubility problems at certain pH levels and other considerations. The melanogenesis promoter metal solution is normally employed at a pH of at least 8. Furthermore, when using the cupric ion at about pH 9 or above, suitably at pH 9.5, no chelating agent is required, because no insoluble traces can be found in the solution. Suitably monoethanolamine or other nitrogen-containing alkalizers, such as other alkanolamines, ammonia, etc. can be used for adjusting the desired pH. Alkali hydroxides work well only if a chelating agent is also employed to maintain the solution. The basic pH has the further advantage of swelling the hair and this allows a better dye take. In the case of using the cupric ion it is decidedly preferable to impregnate the hair first with the solution containing the cupric ion and, after rinsing or blotting the hair, impregnating it with the solution containing the 5,6-dihydroxyindole. The intermediate rinsing or blotting of the hair surface is required to prevent superficial dye formation which can be washed off, since dye formation within the hair shaft itself is desired. As used throughout the specification and the claims, in this context the term "rinsing" is intended to include blotting, wiping and any other method for removing a solution from the hair surface. It requires about 2-20 minutes to dye the hair to the maximum achievable depth of color when using a metal salt promoter for melanogenesis; but when using the cupric ion the time required is at the faster end of even this fast time range. Therefore, as can be seen, use of the cupric ion provides a plurality of benefits over and above those that can be achieved with other melanogenesis promoters.

The solution containing the 5,6-dihydroxyindole is suitably employed at pH of at least 8. It should preferably not exceed 9.5, since the solutions are increasingly unstable at increasing pH. At the conclusion of dyeing the hair black or grey, shampooing is preferred to a mere rinse. This is, because any dye that may have formed on the hair surface may not rinse off and then can later rub off the surface. A shampoo will remove such surface dye and thus prevent ruboff.

The concentration of the 5,6-dihydroxyindole is not critical, but suitably from about 0.5 to about 2% by weight of the solution can be employed for reasons of economy and suitable control over the rate of dyeing. As indicated, the concentrations of the respective ingredients are not critical. Therefore, wherever a concentration is characterized in the specification and the claims as being an "effective amount", this characterization means that the amount employed be sufficient for the intended purpose. Such purpose can be as diverse as a different depth of shade, greater economy in cost of ingredients, different reaction rate, solution stability, and the like. Whatever the purpose, the effectiveness of the amount of an ingredient can be determined by routine experimentation. All percentages throughout the specification and the claims are by weight, unless otherwise specified.

If the shade that is desired is other than black, then the hair, subsequent to dyeing and possible shampooing, is subjected to a lightening step by contacting it with a dilute hydrogen peroxide solution until the desired shade is obtained. Any suitable hydrogen peroxide solution useful in the bleaching or lightening of hair can be employed in this step, however, it was found that an $H_2O_2$ concentration of from about 1% to about 6% is sufficient. In lightening the hair from black or grey, the color will pass through various progressively lighter shades and the process can be stopped by rinsing the hair when it reached the shade that is desired. The natural shade of the hair can be readily re-established after a prior darker shade is no longer desired. The aqueous hydrogen peroxide solution is suitably employed above pH 8, suitably at pH 9. The relatively slow, but not too slow rate of lightening of up to 15 minutes provides sufficient control to the user for stopping at any desired shade or at the natural shade of the hair. In this manner the competing dyeing and bleaching reactions of the prior art and the attendant drawbacks are eliminated to provide a better, more positive control over the entire process, regardless of whether the dyeing is done in the salon or by the user.

The process of the present invention also enables the selective coloring of different portions of the hair to achieve highlights, streaks and other special cosmetic effects.

To maintain stability, suitably the 5,6-dihydroxyindole solution is maintained at an acid pH, advantageously around pH 4.5. Furthermore, the solution at the acid pH should suitably be maintained under anaerobic conditions, such as under nitrogen, whereby during packaging the atmosphere above the solution in the bottle is established with nitrogen rather than air. One method of dealing with the problem is to maintain a small volume of nitrogen above the solution in the bottle, the space being sufficient to allow the addition of an alkalizer before use. This can be, however, inconvenient, and, therefore, suitably a concentrated, such as 12.5%, aqueous alcoholic or entirely alcoholic solution of the 5,6-dihydroxyindole, in which it is easily soluble, can be maintained at acidic pH in a small, full container until it is intended to be used. Immediately before use the contents of this small bottle can be transferred to a larger bottle which can contain a pre-thickened alkaline solution to obtain the alkaline 5,6-dihydroxyindole solution immediately before its use. Another way is to maintain the alkalizer in a small pouch made of a selectively soluble material and then the entire pouch can be dropped into the space above the acidified 5,6-dihydroxyindole-containing solution to avoid the need for the consumer being required to handle a possibly strong alkalizer. Alternatively, when a small, concentrated solution of acidified 5,6-dihydroxyindole is intended to be added to an alkaline solution, then the former could be maintained in a selectively soluble pouch which could in its entirety be transferred to the aqueous alkaline solution to avoid the need of the user having to pour a liquid from one container into another.

It was found that adding a small amount, such as 1% by weight, of a surfactant, such as sodium lauryl sulfate to at least one of the metal and the 5,6-dihydroxyindole solutions, can improve the flow-on properties of the compositions for better applicability to the hair. Similarly, scalp staining can be reduced and the desirable flow properties of the solutions can be improved by adding a small amount, such as 0.5% by weight of a thickener to both of the solutions, such as carbomer 940, a polymer of acrylic acid crosslinked with a polyfunctional agent and sold by the Goodrich Chemical Company under the name of Carbopol 940. The identity of other agents for adjusting desirable flow properties can be determined by routine experimentation, since such flow property-adjusting agents are well known in the field of compounding hair treatment compositions. It is also known in the art of hair treatment compositions that certain flow property-changing additives may be incompatible with certain compositions. It was found, for example, that additives such as cocamidopropyl hydroxysultaine, sold by Lonza Chemical Co. under the name of Lonzaine CS, and hydroxypropyl methylcellulose sold by Dow Chemical Co. under the name Methocel, were apparently not compatible with compositions of the present invention, because the resulting color was not as deep when these materials were included. Other ingredients known per se, such as conditioners, perfumes, anti-static agents and the like, can be included in the compositions or can be subsequently applied to the hair.

The following examples serve as further illustrations of the present invention.

EXAMPLE 1

The following promoter composition was prepared:

| | |
|---|---|
| $CuSO_4.5H_2O$ | 1% |
| carbomer 940 | 0.5% |
| sodium lauryl sulfate | 1% |
| monethanolamine | to pH 9.5 |
| water q.s. to 100 | |

The following dye composition was prepared:

| | |
|---|---|
| sodium acetate | 1.2% |
| 5,6-dihydroxyindole | 1.2% |
| carbomer 940 | 0.47% |
| ethanol | 19.7% |
| sodium hydroxide | to pH 8.5 |

Hair was saturated with the catalytic composition for five minutes and then rinsed with water. Next the hair was saturated with the 5,6-dihydroxyindole-containing composition for a period of 5 minutes. The resulting black dyed hair was shampooed to remove any melanin from the surface of the hair.

EXAMPLE 2

Light brown hair was dyed black with the procedure of Example 1. Subsequently the hair was saturated with a 6% aqueous solution of hydrogen peroxide at pH 9. After 10 minutes when the original light brown shade of the hair was reached, the hair was rinsed. The same procedure was repeated but the hair was lightened for 6 minutes to a darker brown shade. Three weeks later the hair was further lightened for 3½ minutes to its original light brown shade.

EXAMPLE 3

The same process was carried out as in Example 1, on blond hair, except that the concentration of the 5,6-dihydroxyindole was only 0.5%. Dyeing was carried out only for 2 minutes to a light to medium gray color. After shampooing, a 6% aqueous hydrogen peroxide solution at pH 9 was employed to lighten the hair to a light brown shade within 6 minutes.

EXAMPLE 4

The copper sulfate solution of Example 1 was replaced by employing 0.25% $FeSO_4$ based on the composition premixed with citric acid in an amount suitable to prevent precipitation of the iron at alkaline pH, and monethanolamine was used to adjust the pH to 9.5.

The procedure of Example 1 was repeated, except that no carbomer 940 was contained in the 5,6-dihydroxyindole-containing solution. The hair was exposed to the catalyst solution for 10 minutes, then rinsed and saturated with the 5,6-dihydroxyindole-containing solution for 10 minutes until the initially light brown-colored hair turned distinctly darker.

EXAMPLE 5

The same procedure as in Example 1 was repeated, except that the 5,6-dihydroxyindole-containing solution was applied first, followed, after a rinse, by the catalyst-containing solution. The resulting color on the hair was less intense than in the case of Example 1.

We claim:

1. A process for dyeing hair to a given color by melanogenesis of a melanin precursor which is 5,6-dihydroxyindole, the process comprising the steps of:
   (a) first applying to the hair an aqueous alkaline pretreatment solution containing a melanogenesis-promoting transition metal cation for a period of time sufficient to retain a melanogenesis-promoting amount of said metal cation in association with the hair subsequent to rinsing of the hair;
   (b) rinsing the hair, and
   (c) thereafter applying to the rinsed hair an aqueous, alcoholic or hydroalcoholic dye solution containing an effective hair dyeing amount of 5,6-dihydroxyindole for a period of time sufficient for the hair to acquire said given color by melanogenesis.

2. The process of claim 1 wherein the step (c) melanogesis is essentially complete within about 20 minutes following application of the dye solution.

3. The process of claim 2 further comprising the step (d) contacting the hair dyed in accordance with step (c) with a solution of hydrogen peroxide, whereby a color lighter than said given color is obtained.

4. The process of claim 3 wherein the lightening of the hair in step (d) is essentially complete within about 15 minutes following application of the hydrogen peroxide solution.

5. The process of claim 2 or 4 wherein the metal cation is at least one of iron, cobalt, manganese, copper, silver, titanium, zirconium, tantalum, chromium, nickel, palladium, platinum, gold, mercury, cadmium, zinc, tin, antimony, lead, and bismuth.

6. The process of claim 5 wherein the pH of the pretreatment solution is at least 8, and wherein the pH of the dye solution is at least 8.

7. The process of claim 2 or 4 wherein the metal cation is selected from the group consisting of cupric and ferrous cations, and mixtures thereof, and wherein the pH of the pretreatment solution is at least 8.

8. The process of claim 7 wherein the pH of the pretreatment solution is at least 9 and wherein the pH of the dye solution is at least 8.

9. The process of claim 8 wherein the metal cation is the cupric cation.

10. The process of claim 8 wherein the metal cation is the ferrous cation.

11. The process of claim 4 wherein the pH of the hydrogen peroxide solution is at least 8.

12. The hair dyeing process of claim 11 wherein the pH of the pretreatment solution is at least 8, and wherein the pH of the dye solution is at least 8.

13. The process of claim 1 or 3 wherein at least one of said dye solution and said pretreatment solution further comprises at least one of a thickener, surfactant, antistatic additive or perfume.

14. The process of claim 1 or 3 further comprising the step of rinsing or shampooing the hair following step (c).

15. The process of claim 3 further comprising the step of rinsing the hair following step (d).

16. A hair dyeing kit which includes in a single package a plurality of containers, comprising a first container including therein an aqueous alkaline pH solution of an effective amount of a transition metal cation which promotes melanin formation, a second container including therein an aqueous, aqueous-alcoholic, or alcoholic solution of a hair dyeing effective amount of 5,6-dihydroxyindole at an acidic pH, a vapor space being maintained above the solution in said second container and containing a non-oxidizing gas in said space, a third container including therein an alkalizer, said vapor space in said second container being of sufficient volume to accept said third container or the contents of said container within said vapor space, a fourth container which contain an aqueous solution of hydrogen peroxide, said kit being used in accordance with the process of claim 3.

17. A hair dyeing kit which includes in a single package a plurality of containers, a comprising a first container including therein an aqueous alkaline pH solution of an effective amounts of a transition metal cation which promotes melanin formation, a second container including therein an alkaline solution, a vapor space being maintained above the solution, a vapor space being maintained above the solution in said second container, a third container including therein an aqueous, aqueous-alcoholic, or alcoholic solution of a hair dyeing effective amount of 5,6-dihydroxyindole at acidic pH, said vapor space in said second container being of sufficient volume to accept said third container or the contents of said third container within said vapor space, and a fourth container which contains an aqueous solution of hydrogen peroxide, said kit being used in accordance with the process of claim 3.

18. A hair dyeing kit which includes in a single package of plurality of containers, comprising a first container including therein an aqueous alkaline pH solution containing a hair dyeing effective amount of a copper cation, a second container including therein an aqueous, aqueous-alcoholic, or alcoholic solution of an effective amount of 5,6-dihydroxyindole at an acidic pH, a vapor space being maintained above the solution in said second container and containing a non-oxidizing gas in said space, and a third container including therein an alkalizer, said vapor space in said second container being of sufficient volume to accept said third container or the contents of said third container within said vapor space, said kit being used in accordance with the process of claim 1.

19. A hair dyeing kit according to claim 16, wherein the kit further comprises a fourth container which contains an aqueous solution of hydrogen peroxide, said kit being used in accordance with the process of claim 3.

20. A hair dyeing kit which includes in a single package a plurality of containers, comprising a first container including therein an aqueous alkaline pH solution containing an effective amount of a copper cation, a second container including therein an alkaline solution, a vapor space being maintained above the solution in said second container, and a third container including therein an aqueous, aqueous-alcoholic, or alcoholic solution of a hair dyeing effective amount of 5,6-dihydroxyindole at acidic pH, said vapor space in said second container being of sufficient volume to accept said third container or the contents of said third container within said vapor space, said kit being used in accordance with the process of claim 1.

21. A hair dyeing kit according to claim 18, wherein the kit further comprises a fourth container which contains an aqueous solution of hydrogen peroxide, said kit being used in accordance with the process of claim 3.

* * * * *